United States Patent
Sun

(10) Patent No.: US 12,239,095 B2
(45) Date of Patent: Mar. 4, 2025

(54) GRANULE FOR DETECTING OCCULT BLOOD IN PET URINE AND METHOD FOR PREPARING THE SAME

(71) Applicant: Shandong Ruida Silica Gel Co., Ltd., Linyi (CN)

(72) Inventor: Qinbin Sun, Linyi (CN)

(73) Assignee: SHANDONG RUIDA SILICA GEL CO., LTD., Linyi (CN)

( * ) Notice: Subject to any disclaimer, the term of this patent is extended or adjusted under 35 U.S.C. 154(b) by 0 days.

(21) Appl. No.: 18/785,008

(22) Filed: Jul. 26, 2024

(65) Prior Publication Data

US 2025/0008916 A1     Jan. 9, 2025

Related U.S. Application Data

(63) Continuation-in-part of application No. 18/516,887, filed on Nov. 21, 2023.

(30) Foreign Application Priority Data

Jul. 5, 2023 (CN) ......................... 202310816852.7

(51) Int. Cl.
*A01K 1/015* (2006.01)
*G01N 21/78* (2006.01)
*G01N 33/72* (2006.01)

(52) U.S. Cl.
CPC .......... *A01K 1/0154* (2013.01); *A01K 1/0152* (2013.01); *G01N 21/78* (2013.01); *G01N 33/72* (2013.01)

(58) Field of Classification Search
CPC ........................... A01K 1/0154; A01K 1/0152
See application file for complete search history.

(56) References Cited

U.S. PATENT DOCUMENTS

2017/0074864 A1* 3/2017 Jollez ................ B01J 20/28073

FOREIGN PATENT DOCUMENTS

DE     3816225 C2 *   1/1994  ......... A01K 1/0152

* cited by examiner

*Primary Examiner* — Robert J Yamasaki
*Assistant Examiner* — Charles Zoltan Constantine
(74) *Attorney, Agent, or Firm* — MATTHIAS SCHOLL P.C.; Matthias Scholl

(57) ABSTRACT

A granule for detecting occult blood in pet urine including 50-70 parts by weight of an adsorbent, 50-60 parts by weight of a filler, 3-5 parts by weight of an antibacterial agent, 5-10 parts by weight of a deodorant, 2-4 parts by weight of cumene hydroperoxide, and 2-4 parts by weight of an indicator.

4 Claims, No Drawings

GRANULE FOR DETECTING OCCULT BLOOD IN PET URINE AND METHOD FOR PREPARING THE SAME

CROSS-REFERENCE TO RELATED APPLICATIONS

This application is a continuation-in-part of U.S. Ser. No. 18/516,887 filed on Nov. 21, 2023 now, which claims foreign priority to Chinese Patent Application No. 202310816852.7 filed Jul. 5, 2023, the contents of which, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure relates to a granule for detecting occult blood in pet urine and a method for preparing the same.

Pets are good friends that bring happiness and companionship to people. However, pets are prone to diseases, and due to language barriers, when they suffer from serious symptoms, it may be difficult to treat. Hemoglobin content in the urine is an important indicator for health examination of pets. Some pet hospitals may provide checkup services for pets, but the hospitals are thinly distributed, and the fees are expensive.

SUMMARY

To solve the aforesaid problems, the disclosure provides a granule for detecting occult blood in pet urine and a method for preparing the same.

The granule for detecting occult blood in pet urine comprises 50-70 parts by weight of an adsorbent, 50-60 parts by weight of a filler, 3-5 parts by weight of an antibacterial agent, 5-10 parts by weight of a deodorant, 2-4 parts by weight of cumene hydroperoxide, and 2-4 parts by weight of an indicator.

In a class of this embodiment, the adsorbent is activated carbon, activated silica, perlite, or a mixture thereof.

In a class of this embodiment, the filler is modified starch, polyester fiber, acetate fiber, nylon fiber, microcrystalline cellulose, or a mixture thereof.

In a class of this embodiment, the antibacterial agent is polyhexamethylene biguanide hydrochloride, sodium benzoate, potassium sorbate, or a mixture thereof.

In a class of this embodiment, the deodorant is mugwort leaf, grapefruit peel, mulberry leaf, or a mixture thereof.

In a class of this embodiment, the indicator is tetramethylbenzidine.

Further provided is a method for preparing the granule for detecting occult blood in pet urine comprising:
1) weighing the adsorbent, the filler, the antibacterial agent, the deodorant, cumene hydroperoxide, and the indicator according to corresponding weight parts thereof as raw materials;
2) pulverizing each component of the raw materials in 1);
3) drying pulverized components obtained in 2);
4) mixing dried components of the raw materials, feeding to a tablet press machine for granulation, to yield flaky granules; and
5) screening the flaky granules and collecting complete flaky granules.

In a class of this embodiment, after being pulverized, each component is screened using a 100-mesh sieve.

In a class of this embodiment, the pulverized components are dried at 70-80° C. for 1.5-2 hours.

In a class of this embodiment, the complete flaky granules have a diameter of 30 mm, and a thickness of 4 mm; the broken granules after screening are re-crushed and recycled.

The following advantages are associated with the granule for detecting occult blood in pet urine and a method for preparing the same:

The granule is placed in a pet's urine excretion area such as a cat litter basin, so that the granule comes into full contact with urine. If hemoglobin is present in urine, it will be catalyzed by cumene hydroperoxide to produce peroxides. Hydrogen peroxide reacts with the indicator and a different color presents. The level of hemoglobin content can be determined by determining whether the color changes and the intensity of the color.

DETAILED DESCRIPTION

To further illustrate the disclosure, embodiments detailing a granule for detecting occult blood in pet urine and a method for preparing the same are described below. It should be noted that the following embodiments are intended to describe and not to limit the disclosure.

Example 1

1) Weighing 50 g of activated silica, 50 g of acetate fiber, 3 g of polyhexamethylene biguanide hydrochloride, 5 g of mulberry leaves, 2 g of cumene hydroperoxide, and 2 g of tetramethylbenzidine as raw materials;
2) pulverizing each component of the raw materials in 1), and screening the pulverized component using a 100-mesh sieve;
3) drying pulverized components obtained in 2) at 70° C. for 2 hours;
4) mixing dried components of the raw materials, feeding to a tablet press machine for granulation, to yield flaky granules; and
5) screening the flaky granules and collecting complete flaky granules having a diameter of 30 mm and a thickness of 4 mm, to yield granules for detecting occult blood in pet urine.

Example 2

1) Weighing 30 g of activated carbon, 40 g of perlite, 20 g of modified starch, 20 g of nylon fiber, 20 g of microcrystalline cellulose, 1 g of sodium benzoate, 4 g of potassium sorbate, 3 g of mugwort leaf, 7 g of pomelo peel, 4 g of hemoglobin peroxide, and 4 g of tetramethylbenzidine as raw materials;
2) pulverizing each component of the raw materials in 1), and screening the pulverized component using a 100-mesh sieve;
3) drying pulverized components obtained in 2) at 80° C. for 1.5 hours;
4) mixing dried components of the raw materials, feeding to a tablet press machine for granulation, to yield flaky granules; and
5) screening the flaky granules and collecting complete flaky granules having a diameter of 30 mm and a thickness of 4 mm, to yield granules for detecting occult blood in pet urine.

Example 3

1) Weighing 20 g of activated carbon, 20 g of activated silica, 10 g of perlite, 15 g of modified starch, 10 g of polyester fiber, 10 g of acetate fiber, 10 g of nylon fiber, 10 g of microcrystalline cellulose, 1.5 g of polyhexamethylene biguanide hydrochloride, 1 g of sodium benzoate, 1.5 g of potassium sorbate, 2 g of mugwort leaf, 2.5 g of pomelo peel, 3 g of mulberry leaves, 3 g of cumene hydroperoxide, and 3 g of tetramethylbenzidine as raw materials;
2) pulverizing each component of the raw materials in 1), and screening the pulverized component using a 100-mesh sieve;
3) drying pulverized components obtained in 2) at 75° C. for 1.7 hours;
4) mixing dried components of the raw materials, feeding to a tablet press machine for granulation, to yield flaky granules; and
5) screening the flaky granules and collecting complete flaky granules having a diameter of 30 mm and a thickness of 4 mm, to yield granules for detecting occult blood in pet urine.

The granules for detecting occult blood in pet urine prepared in Examples 1-3 were added to 0.15 mmol/L hemoglobin solution, respectively, and the result was that the granules in Examples 1-3 all showed blue. 0.15 mmol/L is the upper limit of the hemoglobin content of normal pet urine, so the granules prepared by the disclosure are able to change to blue through color reaction when the hemoglobin content of the pet's urine exceeds the standard.

It will be obvious to those skilled in the art that changes and modifications may be made, and therefore, the aim in the appended claims is to cover all such changes and modifications.

What is claimed is:

1. A method for preparing granules for detecting occult blood in pet urine comprising:
    a) weighing 50-70 parts by weight of an adsorbent, 50-60 parts by weight of a filler, 3-5 parts by weight of an antibacterial agent, 5-10 parts by weight of a deodorant, 2-4 parts by weight of cumene hydroperoxide, and 2-4 parts by weight of an indicator as raw materials;
    b) pulverizing each component of the raw materials in a);
    c) drying the pulverized components obtained in b);
    d) mixing the dried components of c) and feeding the mixture into a tablet press machine to granulate the mixture and yield flaky granules; and
    e) screening and collecting the flaky granules.
2. The method of claim 1, wherein after being pulverized, each component is screened using a 100-mesh sieve.
3. The method of claim 1, wherein after being pulverized, each component is screened using a 100-mesh sieve.
4. The method of claim 1, wherein the flaky granules have a diameter of 30 mm, and a thickness of 4 mm.

\* \* \* \* \*